(12) United States Patent
Takaishi et al.

(10) Patent No.: US 8,592,438 B2
(45) Date of Patent: Nov. 26, 2013

(54) PLANT DISEASE CONTROL COMPOSITION

(75) Inventors: Masanao Takaishi, Toyonaka (JP);
Norio Kimura, Nishinomiya (JP)

(73) Assignee: Sumitomo Chemical Intellectual Property Service, Ltd, Osaka (JP)

( * ) Notice: Subject to any disclaimer, the term of this patent is extended or adjusted under 35 U.S.C. 154(b) by 295 days.

(21) Appl. No.: 12/922,666

(22) PCT Filed: Mar. 16, 2009

(86) PCT No.: PCT/JP2009/055565
§ 371 (c)(1),
(2), (4) Date: Sep. 14, 2010

(87) PCT Pub. No.: WO2009/116658
PCT Pub. Date: Sep. 24, 2009

(65) Prior Publication Data
US 2011/0021580 A1    Jan. 27, 2011

(30) Foreign Application Priority Data

Mar. 21, 2008  (JP) ................. 2008-073241

(51) Int. Cl.
*A01N 43/54* (2006.01)
*A01N 37/18* (2006.01)
*A01N 37/36* (2006.01)
*A01N 37/42* (2006.01)
*A01P 3/00* (2006.01)

(52) U.S. Cl.
USPC ........... 514/275; 514/513; 514/532; 514/534; 514/538; 514/539; 514/540; 514/542; 514/561; 514/562; 514/563; 514/564; 514/567; 514/617; 514/618; 514/619; 514/621; 514/622

(58) Field of Classification Search
USPC ......... 514/275, 622, 513, 532, 534, 538, 539, 514/540, 542, 561–564, 567, 617–619, 621
See application file for complete search history.

(56) References Cited

U.S. PATENT DOCUMENTS

| | | | |
|---|---|---|---|
| 4,783,459 A | 11/1988 | Buhmann et al. | |
| 4,814,338 A | 3/1989 | Ito et al. | |
| 4,931,560 A | 6/1990 | Hubele | |
| 5,153,200 A * | 10/1992 | Hubele | 514/275 |
| 5,589,479 A | 12/1996 | Eicken et al. | |
| 5,948,819 A * | 9/1999 | Ohtsuka et al. | 514/617 |

FOREIGN PATENT DOCUMENTS

| | | | |
|---|---|---|---|
| DE | 151404 | * | 10/1981 |
| EP | 0 754 672 A1 | | 1/1997 |
| GB | 2 267 644 A | | 12/1993 |
| JP | 62-294665 A | | 12/1987 |
| JP | 6-29263 B2 | | 4/1994 |
| JP | 6-49689 B2 | | 6/1994 |
| JP | 7-165512 A | | 6/1995 |
| WO | WO 95/27693 A1 | | 10/1995 |
| WO | WO 96/07633 A1 | | 3/1996 |

OTHER PUBLICATIONS

Derwent Abstract 1982-03995E, abstracting DD 151404 (Oct. 21, 1981).*
HCAPLUS abstract 1993:185736 (1993).*
HCAPLUS abstract 1991:223405 (1991).*
HCAPLUS abstract 1995:694232 (1995).*
Ichiba, T., et al., "Fungicidal Activities of α-Methoxyphenylacetic Acid Derivatives" Journal of Pesticide Science, vol. 27, No. 2, pp. 118-126, May 2002.

* cited by examiner

*Primary Examiner* — John Pak
(74) *Attorney, Agent, or Firm* — Dickstein Shapiro LLP

(57) ABSTRACT

A plant disease control composition comprising, as an active ingredient, a compound of formula (I) or a salt thereof, and one or more anilinopyrimidine compounds selected from the group consisting of 4,6-dimethyl-N-phenyl-2-pyrimidinamine, 4-methyl-N-phenyl-6-(1-propynyl)-2-pyrimidinamine and 4-cyclopropyl-6-methyl-N-phenyl-2-pyrimidinamine has an excellent plant disease control effect.

(I)

$$\underset{(X)_m}{\phantom{X}}\text{—phenyl—}\overset{R_1}{\underset{\phantom{X}}{CH}}-\overset{Z}{\underset{\phantom{X}}{C}}-Y$$
$$(CH_2)_n-M-Q$$

14 Claims, No Drawings

PLANT DISEASE CONTROL COMPOSITION

TECHNICAL FIELD

The present invention relates to a plant disease control composition and a plant disease control method.

BACKGROUND ART

Plant disease control agents have been variously developed to control plant diseases, however, a plant disease control agent having higher activity is always being demanded.

The present invention has an object of providing a plant disease control composition having high activity, and a method capable of effectively controlling a plant disease.

DISCLOSURE OF THE INVENTION

The present invention provides the followings.

[1] A plant disease control composition comprising Group A and Group B as an active ingredient (hereinafter, referred to as composition of the present invention).

Group A a compound of formula (I) or a salt thereof:

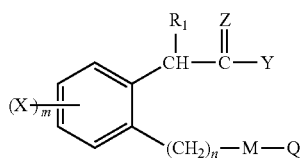

(I)

wherein, $R_1$ represents a halogen atom, optionally substituted alkyl group, optionally substituted hydroxyl group, alkylthio group, alkylsulfinyl group, alkylsulfonyl group, optionally substituted amino group or nitro group, Q represents an optionally substituted aryl group, optionally substituted heterocyclic group, mono- or di-substituted methyleneamino group, optionally substituted (substituted imino)methyl group, optionally substituted alkyl group, optionally substituted alkenyl group, optionally substituted alkynyl group, substituted carbonyl group or substituted sulfonyl group, X represents a halogen atom, optionally substituted alkyl group or optionally substituted hydroxyl group, Y represents an optionally substituted hydroxyl group, alkylthio group or optionally substituted amino group (with the proviso that when $R_1$ represents a hydroxyl group, then, Y is not an alkoxy group), Z represents an oxygen atom or sulfur atom, M represents an oxygen atom, $S(O)_l$ (wherein l represents 0, 1 or 2), $NR_2$ (wherein $R_2$ represents a hydrogen atom, alkyl group or acyl group) or single bond, n represents 0, 1 or 2, m represents 0, 1, 2 or 3;

(hereinafter, referred to as compound (I))

Group B one or more anilinopyrimidine compounds selected from the group consisting of 4,6-dimethyl-N-phenyl-2-pyrimidinamine (hereinafter, referred to as compound (II)), 4-methyl-N-phenyl-6-(1-propynyl)-2-pyrimidinamine (hereinafter, referred to as compound (III)) and 4-cyclopropyl-6-methyl-N-phenyl-2-pyrimidinamine (hereinafter, referred to as compound (IV)).

[2] The plant disease control composition according to [1], wherein Group A is a compound of formula (I) or a salt thereof, and in the compound of formula (I), $R_1$ represents a halogen atom, or a hydroxyl group optionally substituted with a C1 to C4 alkyl group or C1 to C4 haloalkyl group, Q represents a phenyl group optionally substituted with one or more of halogen atoms, methyl groups, trifluoromethyl groups or methoxy groups, Y represents an amino group optionally substituted with one or more of C1 to C3 alkyl groups, Z represents an oxygen atom, M represents an oxygen atom, n represents 1, m represents 0.

[3] The plant disease control composition according to [1], wherein Group A is a compound of formula (I) or a salt thereof, and in the compound of formula (I), $R_1$ represents a methoxy group, Q represents a 2,5-dimethylphenyl group, Y represents a monomethylamino group, Z represents an oxygen atom, M represents an oxygen atom, n represents 1, m represents 0.

[4] The plant disease control composition according to any one of [1] to [3], wherein Group B is 4,6-dimethyl-N-phenyl-2-pyrimidinamine.

[5] The plant disease control composition according to any one of [1] to [3], wherein Group B is 4-methyl-N-phenyl-6-(1-propynyl)-2-pyrimidinamine.

[6] The plant disease control composition according to any one of [1] to [3], wherein Group B is 4-cyclopropyl-6-methyl-N-phenyl-2-pyrimidinamine.

[7] The plant disease control composition according to any one of [1] to [6], wherein the weight ratio of Group A to Group B is in the range from 0.125:1 to 20:1.

[8] A plant disease control method comprising applying Group A and Group B to a plant or the soil where a plant is grown (hereinafter, referred to as control method of the present invention)

Group A a compound of formula (I) or a salt thereof:

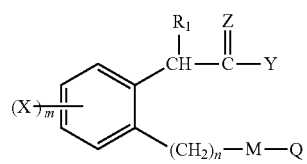

(I)

wherein, $R_1$ represents a halogen atom, optionally substituted alkyl group, optionally substituted hydroxyl group, alkylthio group, alkylsulfinyl group, alkylsulfonyl group, optionally substituted amino group or nitro group, Q represents an optionally substituted aryl group, optionally substituted heterocyclic group, mono- or di-substituted methyleneamino group, optionally substituted (substituted imino)methyl group, optionally substituted alkyl group, optionally substituted alkenyl group, optionally substituted alkynyl group, substituted formyl group or substituted sulfonyl group, X represents a halogen atom, optionally substituted alkyl group or optionally substituted hydroxyl group, Y represents an optionally substituted hydroxyl group, alkylthio group or optionally substituted amino group (with the proviso that when $R_1$ represents a hydroxyl group, then, Y is not an alkoxy group), Z represents an oxygen atom or sulfur atom, M represents an oxygen atom, $S(O)_l$ (wherein l represents 0, 1 or 2), $NR_2$ (wherein $R_2$ represents a hydrogen atom, alkyl group or acyl group) or single bond, n represents 0, 1 or 2, m represents 0, 1, 2 or 3;

Group B one or more anilinopyrimidine compounds selected from the group consisting of 4,6-dimethyl-N-phenyl-2-pyrimidinamine, 4-methyl-N-phenyl-6-(1-propynyl)-2-pyrimidinamine and 4-cyclopropyl-6-methyl-N-phenyl-2-pyrimidinamine.

[9] The plant disease control method according to [8], wherein Group A is a compound of formula (I) or a salt thereof, and in the compound of formula (I), $R_1$ represents a halogen atom, or a hydroxyl group optionally substituted with a C1 to C4 alkyl group or C1 to C4 haloalkyl group, Q represents a phenyl group optionally substituted with one or more of halogen atoms, methyl groups, trifluoromethyl groups or methoxy groups, Y represents an amino group optionally substituted with one or more of C1 to C3 alkyl groups, Z represents an oxygen atom, M represents an oxygen atom, n represents 1, m represents 0.

[10] The plant disease control method according to [8], wherein Group A is a compound of formula (I) or a salt thereof, and in the compound of formula (I), $R_1$ represents a methoxy group, Q represents a 2,5-dimethylphenyl group, Y represents a monomethylamino group, Z represents an oxygen atom, M represents an oxygen atom, n represents 1, m represents 0.

[11] The plant disease control method according to any one of [8] to [10], wherein Group B is 4,6-dimethyl-N-phenyl-2-pyrimidinamine.

[12] The plant disease control method according to any one of [8] to [10], wherein Group B is 4-methyl-N-phenyl-6-(1-propynyl)-2-pyrimidinamine.

[13] The plant disease control method according to any one of [8] to [10], wherein Group B is 4-cyclopropyl-6-methyl-N-phenyl-2-pyrimidinamine.

[14] The plant disease control method according to any one of [8] to [13], wherein the weight ratio of Group A to Group B is in the range from 0.125:1 to 20:1.

[15] Use of a mixture of Group A and Group B for controlling a plant disease.

Group A a compound of formula (I) or a salt thereof:

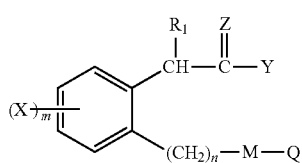

(I)

wherein, $R_1$ represents a halogen atom, optionally substituted alkyl group, optionally substituted hydroxyl group, alkylthio group, alkylsulfinyl group, alkylsulfonyl group, optionally substituted amino group or nitro group, Q represents an optionally substituted aryl group, optionally substituted heterocyclic group, mono- or di-substituted methyleneamino group, optionally substituted (substituted imino)methyl group, optionally substituted alkyl group, optionally substituted alkenyl group, optionally substituted alkynyl group, substituted formyl group or substituted sulfonyl group, X represents a halogen atom, optionally substituted alkyl group or optionally substituted hydroxyl group, Y represents an optionally substituted hydroxyl group, alkylthio group or optionally substituted amino group (with the proviso that when $R_1$ represents a hydroxyl group, then, Y is not an alkoxy group), Z represents an oxygen atom or sulfur atom, M represents an oxygen atom, $S(O)_l$ (wherein, l represents 0, 1 or 2), $NR_2$ (wherein, $R_2$ represents a hydrogen atom, alkyl group or acyl group) or single bond, n represents 0, 1 or 2, m represents 0, 1, 2 or 3;

Group B one or more anilinopyrimidine compounds selected from the group consisting of 4,6-dimethyl-N-phenyl-2-pyrimidinamine, 4-methyl-N-phenyl-6-(1-propynyl)-2-pyrimidinamine and 4-cyclopropyl-6-methyl-N-phenyl-2-pyrimidinamine.

In the compound (I) of formula (I), "the halogen atom" represented by $R_1$ includes fluorine, chlorine, bromine or iodine.

"The optionally substituted alkyl group" represented by $R_1$ means an alkyl group in which a hydrogen atom of the alkyl group may be substituted with an atom other than a hydrogen atom or with a functional group. Examples of "the alkyl group" represented by $R_1$ include alkyl groups having 1 to 8 carbon atoms, preferably alkyl groups having 1 to 4 carbon atoms. Specific examples of "the alkyl group" of "the optionally substituted alkyl group" represented by $R_1$ include a methyl group, ethyl group, propyl group, isopropyl group, butyl group, isobutyl group, tert-butyl group, pentyl group and hexyl group.

Among of them, a methyl group and ethyl group are listed as a particularly preferable alkyl group.

Examples of "the optionally substituted alkyl group" represented by $R_1$ include haloalkyl groups (for example, difluoromethyl group, trifluoromethyl group, chloromethyl group, 2-bromoethyl group and 2,3-dichloropropyl group) in which a hydrogen atom of the alkyl group is substituted with a halogen atom (for example, fluorine atom, chlorine atom, bromine atom and iodine atom); and alkoxyalkyl groups (for example, methoxymethyl group, ethoxymethyl group and methoxyethyl group) in which a hydrogen atom of the alkyl group is substituted with an alkoxy group having 1 to 8 carbon atoms, preferably an alkoxy group having 1 to 4 carbon atoms (for example, methoxy group, ethoxy group, propoxy group and butoxy group).

Among of them, a trifluoromethyl group and methoxymethyl group are listed as a preferable optionally substituted alkyl group.

"The optionally substituted hydroxyl group" represented by $R_1$ means a hydroxyl group in which a hydrogen atom of the hydroxyl group may be substituted with an atom other than a hydrogen atom or with a functional group. Examples of "the optionally substituted hydroxyl group" represented by $R_1$ include a hydroxyl group, alkoxy group, alkenyloxy group, alkynyloxy group, alkylcarbonyloxy group, (alkylthio)carbonyloxy group, alkylsulfonyloxy group, arylsulfonyloxy group, mono or di-alkyl-substituted carbamoyloxy group, aryloxy group and tetrahydropyranyloxy group.

Examples of "the alkylthio group" represented by $R_1$ include alkylthio groups having 1 to 8 carbon atoms, preferably alkylthio groups having 1 to 4 carbon atoms. Specific examples of "the alkylthio group" represented by $R_1$ include a methylthio group, ethylthio group, propylthio group and butylthio group.

Among of them, a methylthio group is mentioned as a preferable alkylthio group.

Examples of "the alkylsulfinyl group" represented by $R_1$ include alkylsulfinyl groups having 1 to 8 carbon atoms, preferably alkylsulfinyl groups having 1 to 4 carbon atoms. Specific examples of "the alkylsulfinyl group" represented by $R_1$ include a methylsulfinyl group, ethylsulfinyl group and propylsulfinyl group.

Among of them, a methylsulfinyl group is mentioned as a preferable alkylsulfinyl group.

Examples of "the alkylsulfonyl group" represented by $R_1$ include alkylsulfonyl groups having 1 to 8 carbon atoms, preferably alkylsulfonyl groups having 1 to 4 carbon atoms. Specific examples of "the alkylsulfonyl group" represented by $R_1$ include a methylsulfonyl group, ethylsulfonyl group and propylsulfonyl group.

Among of them, a methylsulfonyl group is mentioned as a preferable alkylsulfonyl group.

"The optionally substituted amino group" represented by $R_1$ means an amino group in which a hydrogen atom of the amino group may be substituted with an atom other than a hydrogen atom or with a functional group. Examples of "the optionally substituted amino group" represented by $R_1$ include an amino group, amino groups substituted with one or two alkyl groups having 1 to 8 carbon atoms (for example, monomethylamino group, dimethylamino group and monoethylamino group), amino group substituted with a formyl group, and amino groups substituted with an alkylcarbonyl group having 2 to 4 carbon atoms (for example, methylcarbonylamino group). Among of them, amino groups substituted with one alkyl group having 1 to 4 carbon atoms are mentioned as a preferable optionally substituted amino group, and a monomethylamino group is mentioned as a particularly preferable optionally substituted amino group.

Examples of $R_1$ include halogen atoms, alkyl groups, haloalkyl groups, alkoxyalkyl groups, hydroxyl group, alkoxy groups, alkenyloxy groups, alkynyloxy groups, haloalkoxy groups, haloalkenyloxy groups, haloalkynyloxy groups, alkoxyalkoxy groups, alkylcarbonyloxy groups, (alkylthio) carbonyloxy groups, alkylsulfonyloxy groups, arylsulfonyloxy groups, carbamoyloxy groups substituted with one or two alkyls, aryloxy groups, alkylthio groups, alkylsulfinyl groups, alkylsulfonyl groups, amino groups optionally substituted with an alkyl group, nitro group and tetrahydropyranyloxy group. Preferable substituents represented by $R_1$ include halogen atoms, C1 to C4 alkoxy groups, C1 to C4 haloalkoxy groups and hydroxyl group. Among of them, a methoxy group is mentioned as a particularly preferable $R_1$.

"The optionally substituted aryl group" represented by Q means an aryl group in which a hydrogen atom of the aryl group may be substituted with an atom other than a hydrogen atom or with a functional group. Examples of the aryl group of "the optionally substituted aryl group" represented by Q include aryl group having 6 to 14 carbon atoms. Specific examples of the aryl group of "the optionally substituted aryl group" represented by Q include a phenyl group and naphthyl group.

The substituent on the aryl group of "the optionally substituted aryl group" represented by Q includes lower alkyl groups (for example, methyl group, ethyl group, propyl group and butyl group), lower alkenyl groups (for example, vinyl group, allyl group and crotyl group), lower alkynyl groups (for example, ethynyl group, propargyl group and butynyl group), cycloalkyl groups (for example, cyclopropyl group, cyclopentyl group and cyclohexyl group), lower alkoxy lower alkyl groups (for example, methoxymethyl group, ethoxymethyl group and 2-methoxyethyl group), cycloalkenyl groups (for example, cyclopentenyl group and cyclohexenyl group), lower alkanoyl groups (for example, acetyl group, propionyl group and isobutyryl group), lower alkylsilyl groups (for example, trimethylsilyl group, triethylsilyl group, tripropylsilyl group and tributylsilyl group), halo(lower)alkyl groups (for example, difluoromethyl group, trifluoromethyl group, chloromethyl group, 2-bromoethyl group and 2,3-dichloropropyl group), di(lower) alkylamino groups (for example, dimethylamino group and diethylamino group), phenyl group, phenyl(lower)alkyl groups (for example, benzyl group and phenetyl group), phenyl(lower)alkenyl groups (for example, styryl group and cinnamyl group), furyl(lower) alkyl groups (for example, 3-furylmethyl group and 2-furylethyl group), furyl (lower) alkenyl groups (for example, 3-furylvinyl group and 2-furylaryl group), halogen atoms (for example, fluorine atom, chlorine atom, bromine atom and iodine atom), nitro group, cyano group, lower alkylthio groups (for example, methylthio group, ethylthio group and propylthio group), lower alkoxycarbonyl groups (for example, methoxycarbonyl group, ethoxycarbonyl group and propoxycarbonyl group), formyl group, amino group, mono (lower)alkylamino groups (for example, methylamino group and ethylamino group),

—OR

[wherein, R represents a hydrogen atom, lower alkyl group (for example, methyl group, ethyl group, propyl group and butyl group), lower alkenyl group (for example, vinyl group, allyl group and crotyl group), lower alkynyl group (for example, ethynyl group, 2-propynyl group and 3-butynyl), halo(lower)alkyl group (for example, difluoromethyl group, trifluoromethyl group, chloromethyl group, 2-bromoethyl group and 2,3-dichloropropyl group), lower alkanoyl group (for example, acetyl group, propionyl group and butyryl group), phenyl group, lower alkoxyphenyl group (for example, 3-methoxyphenyl group and 4-ethoxyphenyl group), nitrophenyl group (for example, 3-nitrophenyl group and 4-nitrophenyl group), phenyl(lower)alkyl group (for example, benzyl group, phenetyl group and phenyl-propyl group), cyanophenyl (lower) alkyl group (for example, 3-cyanophenylmethyl group and 4-cyanophenylethyl group), benzoyl group, tetrahydropyranyl group, pyridyl group, trifluoromethylpyridyl group, pyrimidinyl group, benzothiazolyl group, quinolyl group, benzoyl (lower) alkyl group (for example, benzoylmethyl group and benzoylethyl group), benzenesulfonyl group, or lower alkylbenzenesulfonyl group (for example, toluenesulfonyl group)],

—CH$_2$-G-R'

[wherein, G represents —O—, —S—, or NR"— (wherein, R" represents a hydrogen atom or lower alkyl group), R' represents a phenyl group, phenyl group substituted with a halogen atom (for example, 2-chlorophenyl group, 4-fluorophenyl group and the like), lower alkoxyphenyl group (for example, 2-methoxyphenyl group, 4-ethoxyphenyl group and the like), pyridyl group, or pyrimidinyl group], and the like.

Here, lower means 1 to 8 carbon atoms, preferably 1 to 6 carbon atoms, further preferably 1 to 4 carbon atoms.

"The optionally substituted aryl group" represented by Q includes phenyl groups optionally substituted with at least one group selected from the group consisting of, for example, halogen atoms, methyl group, trifluoromethyl group and methoxy group. Specific examples of "the optionally substituted aryl group" represented by Q include a 2,5-dimethylphenyl group.

"The optionally substituted heterocyclic group" represented by Q means a heterocyclic group in which a hydrogen atom connected to a ring constituent atom of the heterocyclic group may be substituted with an atom other than a hydrogen atom or with a functional group. Examples of "the optionally substituted heterocyclic group" represented by Q include 5 to 7-membered heterocyclic groups containing, as a ring constituent atom, one to four hetero atoms selected from the group consisting of nitrogen, oxygen and sulfur. These heterocyclic groups may further form a condensed ring together with another hetero ring or benzene ring.

Specific examples of "the optionally substituted heterocyclic group" represented by Q include optionally substituted pyridyl groups (for example, pyridin-2-yl group and pyridin-3-yl group), optionally substituted pyrimidinyl groups (for example, pyrimidin-4-yl group and pyrimidin-2-yl group), optionally substituted quinolyl groups (for example, quinolin-4-yl group), optionally substituted quinazolinyl groups (for example, quinazolin-4-yl group), optionally substituted benzothiazolyl groups (for example, benzothiazol-2-yl group), and optionally substituted pyrazolyl groups (for example, pyrazol-5-yl group).

Among of them, optionally substituted pyridyl groups are mentioned as a preferable optionally substituted heterocyclic group.

As the substituent of "the optionally substituted heterocyclic group" represented by Q, listed are substituents exemplified above as "the optionally substituted aryl group" represented by Q.

Examples of "the mono-substituted or di-substituted methyleneamino group" represented by Q include
formula (a):

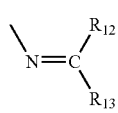

(a)

[wherein, $R_{12}$ and $R_{13}$ are the same or different and represent a hydrogen atom, optionally substituted alkyl group, acyl group, alkylthio group, alkylsulfinyl group, alkylsulfonyl group, optionally substituted amino group, cycloalkyl group, optionally substituted aryl group or optionally substituted heterocyclic group].

"The optionally substituted alkyl group" represented by $R_{12}$ or $R_{13}$ in formula (a) means an alkyl group in which a hydrogen atom of the alkyl group may be substituted with an atom other than a hydrogen atom or with a functional group. As "the optionally substituted alkyl group" represented by $R_{12}$ or $R_{13}$, for example, the same groups of as "the alkyl group" or "the substituted alkyl group" exemplified as $R_1$ are mentioned. Among of them, a methyl group and ethyl group are preferable as the optionally substituted alkyl group represented by $R_{12}$ or $R_{13}$.

As "the acyl group" represented by $R_{12}$ and $R_{13}$, for example, alkylcarbonyl groups and arylcarbonyl groups are mentioned. Examples of the alkylcarbonyl group include C1 to C6 alkylcarbonyl groups, preferably C1 to C4 alkylcarbonyl groups. Specific examples of the alkylcarbonyl group include an acetyl group, trifluoroacetyl group, propionyl group and butyryl group. Examples of the arylcarbonyl group include C6-14 arylcarbonyl groups. Specific examples of the arylcarbonyl group include a benzoyl group and naphthoyl group.

As "the alkylthio group, alkylsulfinyl group, alkylsulfonyl group, optionally substituted amino group" represented by $R_{12}$ and $R_{13}$, for example, the same groups as the alkylthio group, alkylsulfinyl group, alkylsulfonyl group and optionally substituted amino group exemplified for $R_1$ are mentioned.

"The cycloalkyl group" represented by $R_{12}$ and $R_{13}$ includes cycloalkyl groups having 3 to 7 carbon atoms, preferably cycloalkyl groups having 5 to 6 carbon atoms. Specific examples of "the cycloalkyl group" represented by $R_{12}$ and $R_{13}$ include a cyclopropyl group, cyclobutyl group, cyclopentyl group, cyclohexyl group and cycloheptyl group.

"The optionally substituted aryl group" represented by $R_{12}$ and $R_{13}$ means an aryl group in which a hydrogen atom of the aryl group may be substituted with an atom other than a hydrogen atom or with a functional group. Examples of the aryl group of "the optionally substituted aryl group" represented by Q include aryl groups having 6 to 14 carbon atoms. Specific examples of the aryl group of "the optionally substituted aryl group" represented by Q include aryl groups having 6 to 14 carbon atoms, specifically, a phenyl group, naphthyl groups (for example, 1-naphthyl group and the like) and fluorenyl group. Among of them, a phenyl group is preferable as the optionally substituted aryl group represented by Q.

Examples of the substituent of "the optionally substituted aryl group" represented by Q include halogen atoms, optionally substituted alkyl groups, optionally substituted hydroxyl group, alkylthio groups, optionally substituted amino groups, nitro group, phenyl group and cyano group.

Examples of the halogen atom as the substituent of "the optionally substituted aryl group" represented by $R_{12}$ or $R_{13}$ include fluorine, chlorine, bromine and iodine.

As the optionally substituted alkyl group as the substituent of "the optionally substituted aryl group" represented by $R_{12}$ or $R_{13}$, for example, the same groups as "the optionally substituted alkyl group" represented by $R_1$ are mentioned. Examples of the optionally substituted alkyl group as the substituent of "the optionally substituted aryl group" represented by $R_{12}$ or $R_{13}$ include alkyl groups and haloalkyl groups. Specific examples of the optionally substituted alkyl group as the substituent of "the optionally substituted aryl group" represented by $R_{12}$ or $R_{13}$ include a methyl group and trifluoromethyl group.

Examples of the optionally substituted hydroxyl group as the substituent of "the optionally substituted aryl group" represented by $R_{12}$ or $R_{13}$ include a hydroxyl group, alkoxy groups, alkenyloxy groups, alkynyloxy groups, haloalkoxy groups and aryloxy groups.

Examples of the alkoxy group include alkoxy groups having 1 to 8 carbon atoms, preferably alkoxy groups having 1 to 4 carbon atoms. Specific examples of the alkoxy group include a methoxy group, ethoxy group, propoxy group and butoxy group. Among of them, a methoxy group is preferable as the alkoxy group.

Examples of the alkenyloxy group include alkenyloxy groups having 2 to 8 carbon atoms, preferably alkenyloxy groups having 2 to 4 carbon atoms. Specific examples of the alkenyloxy group include a vinyloxy group, allyloxy group and crotyloxy group. Among of them, an allyloxy group is preferable as the alkenyloxy group.

Examples of the alkynyloxy group include alkynyloxy groups having 2 to 8 carbon atoms, preferably alkynyloxy groups having 2 to 4 carbon atoms. Specific examples of the alkynyloxy group include an ethynyloxy group, propargyloxy group and butynyloxy group. Among of them, a propargyloxy is preferable as the alkynyloxy group.

Examples of the haloalkoxy group include a difluoromethoxy group, trifluoromethoxy group and chloromethoxy group. Among of them, a difluoromethoxy is preferable as the haloalkoxy group.

Examples of the aryloxy group include aryloxy groups having 6 to 12 carbon atoms, preferably aryloxy groups having 6 to 8 carbon atoms. Specific examples of the aryloxy group include a phenoxy group and naphthoxy group.

Examples of the alkylthio group as the substituent of "the optionally substituted aryl group" represented by $R_{12}$ or $R_{13}$ include alkylthio groups having 1 to 8 carbon atoms, preferably alkylthio groups having 1 to 4 carbon atoms, further preferably alkylthio groups having 1 to 2 carbon atoms.

Specific examples of the alkylthio group as the substituent of "the optionally substituted aryl group" represented by $R_{12}$ or $R_{13}$ include a methylthio group, ethylthio group, propylthio group and butylthio group. Of then, a methylthio group is preferable as the alkylthio group as the substituent of "the optionally substituted aryl group" represented by $R_{12}$ or $R_{13}$.

Examples of the optionally substituted amino group as the substituent of "the optionally substituted aryl group" represented by $R_{12}$ or $R_{13}$ include an amino group and amino groups substituted with one or two alkyl groups having 1 to 8 carbon atoms (for example, monomethylamino group, dimethylamino group and monoethylamino group).

Examples of the heterocyclic group of "the optionally substituted heterocyclic group" represented by $R_{12}$ or $R_{13}$ include heterocyclic groups in which 1 to 4 hetero atoms, preferably 1 to 2 hetero atoms (for example, oxygen, nitrogen and sulfur) are ring constituent atoms. Specific examples of the heterocyclic group of "the optionally substituted heterocyclic group" include a pyridyl group, pyridazinyl group, pyrazolyl group, pyrimidinyl group, furyl group, thienyl group, oxazolyl group, isooxazolyl group, benzothiazolyl group, quinolyl group, quinazolinyl group, pyrazinyl group, morpholino group and piperazinyl group. Among of them, furyl groups (for example, 2-furyl group), thienyl groups (for example, 2-thienyl group), pyridyl groups (for example, 2-pyridyl group), pyrazinyl groups (for example, 2-pyrazinyl group), pyrimidinyl groups (for example, 2-pyrimidinyl group) and morpholino group are preferable as the heterocyclic group of "the optionally substituted heterocyclic group". As the substituent of "the optionally substituted heterocyclic group", for example, the same groups as the substituent of "the optionally substituted aryl group" represented by $R_{12}$ or $R_{13}$ are mentioned.

"The optionally substituted (substituted iminomethyl group)" represented by Q is, for example, represented by formula (b):

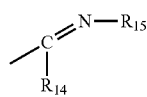

(b)

[wherein, $R_{14}$ and $R_{15}$ have the same meanings as for $R_{12}$ and $R_{13}$, respectively].

As the alkyl group of "the optionally substituted alkyl group" represented by Q, the above-described alkyl groups represented by $R_1$ are mentioned.

Examples of the alkenyl group of "the optionally substituted alkenyl group" represented by Q include alkenyl groups having 2 to 8 carbon atoms, preferably alkenyl groups having 3 to 6 carbon atoms. Specific examples of the alkenyl group of "the optionally substituted alkenyl group" represented by Q include an allyl group, propenyl group, isopropenyl group, butenyl group, isobutenyl group, pentenyl group, hexenyl group and hexadienyl group.

Examples of the alkynyl group of "the optionally substituted alkynyl group" represented by Q include alkynyl groups having 2 to 6 carbon atoms, preferably alkynyl groups having 2 to 4 carbon atoms. Specific examples of the alkynyl group of "the optionally substituted alkynyl group" represented by Q include a propargyl group, ethynyl group and butynyl group. Examples of the substituent of these alkyl groups, alkenyl groups and alkynyl groups include halogen atoms, alkoxy groups, alkylthio groups, alkylsulfinyl groups, alkylsulfonyl groups, substituted amino groups, optionally substituted phenyl groups, optionally substituted naphthyl groups and optionally substituted heterocyclic groups.

"The substituted formyl group" represented by Q means a group in which a hydrogen atom of the formyl group is substituted with an atom other than a hydrogen atom or with a functional group. Examples of "the substituted formyl group" represented by Q include (optionally substituted alkyl)carbonyl groups, (optionally substituted phenyl)carbonyl groups, (optionally substituted naphthyl)carbonyl groups and (optionally substituted heterocyclic group)carbonyl groups.

"The substituted sulfino group" represented by Q means a group in which a hydrogen atom of the sulfino group is substituted with an atom other than a hydrogen atom or with a functional group. Examples of "the substituted sulfino group" represented by Q include (optionally substituted alkyl)sulfonyl groups, (optionally substituted phenyl)sulfonyl groups, (optionally substituted naphthyl)sulfonyl groups and (optionally substituted heterocyclic group)sulfonyl groups.

As "the optionally substituted alkyl group" as the substituent of these "substituted formyl groups" or "substituted sulfino groups", for example, groups exemplified above as "the optionally substituted alkyl group" represented $R_1$ are mentioned. As "the optionally substituted phenyl group", "the optionally substituted naphthyl group" and "the optionally substituted heterocyclic group" as the substituent of "the substituted formyl group" or "the substituted sulfino group", the same groups as the groups exemplified for Q are mentioned respectively.

A 2,5-dimethylphenyl group is a preferable group as Q.

As "the halogen atom, optionally substituted alkyl group and optionally substituted hydroxyl group" represented by X, the same groups as "the halogen atom, optionally substituted alkyl group and optionally substituted hydroxyl group" represented by $R_1$ are mentioned, respectively.

As "the optionally substituted hydroxyl group" and "the alkylthio group" represented by Y, the same groups as "the optionally substituted hydroxyl group" and "the alkylthio group" represented by $R_1$ are mentioned, respectively.

Among of them, a methoxy group is preferable as the optionally substituted hydroxyl group represented by Y.

"The optionally substituted amino group" represented by Y is, for example, a group of the general formula (II):

$$-NR_5R_6 \qquad\qquad\qquad (II)$$

[wherein, $R_5$ represents a hydrogen atom or alkyl group; $R_6$ represents a hydrogen atom, alkyl group or hydroxyalkyl group].

As "the alkyl group" represented by $R_5$ or $R_6$ and as "the alkyl group" of "the hydroxylalkyl group" represented by $R_6$, the same groups as the alkyl group represented by $R_1$ are mentioned.

Examples of Y include C1 to C3 alkoxy groups and groups of the above-described general formula (II). Specific examples of Y include a methoxy group and mono C1 to C3 alkylamino groups (for example, monomethylamino group).

Examples of M include an oxygen atom, sulfur atom and group represented by $NR_2$.

As "the alkyl group" represented by $R_2$, for example, the same groups as the alkyl group represented by $R_1$ are mentioned.

Among of them, a methyl group is preferable as "the alkyl group" represented by $R_2$.

Examples of "the acyl group" represented by $R_2$ include a formyl group; formyl groups substituted with an alkyl group having 1 to 8 carbon atoms, preferably formyl groups substituted with an alkyl group having 1 to 4 carbon atoms (for example, acetyl group, propionyl group and butyryl group); and benzoyl group.

Among of them, an acetyl group is preferable as "the acyl group" represented by $R_2$.

Embodiments of the compound (I) include the following compounds.

[1] A compound of formula (I) in which
$R_1$ represents a halogen atom, or a hydroxyl group optionally substituted with a C1 to C4 alkyl group or C1 to C4 haloalkyl group,
Q represents a phenyl group optionally substituted with at least one group selected from the group consisting of halogen atoms, methyl group, trifluoromethyl group and methoxy group,
Y represents an amino group optionally substituted with one or more of C1 to C3 alkyl groups,
Z represents an oxygen atom,
M represents an oxygen atom,
m represents 0,
n represents 1.

[2] A compound of formula (I) in which
$R_1$ represents a methoxy group,
Q represents a 2,5-dimethylphenyl group,
Y represents a methylamino group,
Z represents an oxygen atom,
M represents an oxygen atom,
m represents 0,
n represents 1.

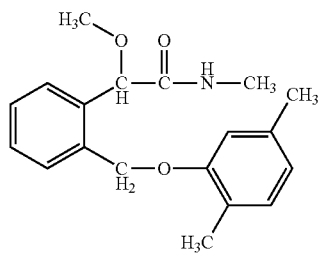 [SMILES: CNC(=O)C(OC)c1ccccc1COc1cc(C)ccc1C]

The compounds of formula (I) and salts thereof are compounds described in WO95-27693-A1. The compounds of formula (I) and salts thereof can be synthesized by a method described in WO95-27693-A1.

The compound (II) is a compound described in JP-A No. 62-294665, and known under the common name of pyrimethanil.

The compound (III) is a compound described in JP-B No. 6-29263, and known under the common name of mepanipyrim.

The compound (IV) is a compound described in JP-B No. 6-49689, and known under the common name of cyprodinil.

The composition of the present invention can be used for controlling plant diseases in cultivated fields such as a field, paddy field, turf, fruit orchard and the like. The composition of the present invention is capable of controlling diseases of crops, without causing chemical injury on the crops, in cultivated fields for cultivating crops listed below.

Agricultural crops: corn, rice, wheat, barley, rye, oat, sorghum, cotton, soybean, peanut, sarrazin, sugar beet, rapeseed, sunflower, sugar cane, tobacco, etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid, etc.;

Flowering plants;

Ornamental foliage plants;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut palm, etc.;

Trees other than fruit trees: tea, mulberry, flowering trees, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), etc.

The above-described "crops" include also plants having resistance to a herbicide such as an HPPD inhibitor such as isoxaflutole and the like, an ALS inhibitor such as imazethapyr or thifensulfuron-methyl and the like, an EPSP synthesizing enzyme inhibitor such as glyphosate and the like, a glutamine synthesizing enzyme inhibitor such as glufosinate and the like, an acetyl CoA carboxylase inhibitor such as sethoxydim and the like, a PPO inhibitor such as flumioxazin and the like; and bromoxynil, dicamba, 2,4-D and the like, which resistance has been imparted by a classical breeding method or a genetic engineering technique.

Examples of the "crop" having the resistance imparted by a classical breeding method include rapeseed, wheat, sunflower and paddy having a resistance to imidazoline ALS inhibiting herbicides such as imazethapyr and the like, and these are already marketed under the trade name of Clearfield (registered trademark). Likewise, there is soybean endowed with resistance to sulfonylurea ALS-inhibiting herbicides such as thifensulfuron methyl and the like by classical breeding methods, and it is already marketed under the trade name of STS soybean. Likewise, examples of the plants endowed with resistance to acetyl CoA carboxylase inhibitors such as trione oximes, aryloxyphenoxypropionic acid herbicides and the like by classical breeding methods include SR corn, and the like. The plants endowed with resistance to acetyl CoA carboxylase inhibitors are described in Proc. Natl. Acad. Sci. USA, vol. 87, pp. 7175 to 7179 (1990) and the like. Further, mutated acetyl CoA carboxylases which are resistant to acetyl CoA carboxylase inhibitors are reported in Weed Science, vol. 53, pp. 728 to 746 (2005) and the like, and plants which are resistant to acetyl CoA carboxylase inhibitors can be produced by introducing such a mutated acetyl CoA carboxylase gene into a plant by a gene recombination technology or introducing a mutation correlated with resistance impartation into a plant acetyl CoA carboxylase. Further, plants which are resistant to acetyl CoA carboxylase inhibitors and ALS inhibitor and the like can be produced by introducing a base substitution mutation-introduced nucleic acid typified by chimera plasty technology (Gura T. 1999. Repairing the Genome's Spelling Mistakes. Science 285: 316-318) into a plant cell thereby introducing a site-specific amino acid substitution mutation into the acetyl CoA carboxylase gene and ALS gene and the like of the plant.

Examples of the plants endowed with resistance by gene recombination technologies include corn, soybean, cotton, rapeseed and beet plant varieties which are resistant to glyphosate, and these are already marketed under the trade name of Round up Ready (registered trademark), AgrisureGT and the like. Likewise, there are corn, soybean, cotton and rapeseed plant varieties endowed with resistance to glufosinate by gene recombination technologies, and these are already marketed under the trade name of Liberty Link (registered trademark) and the like. Likewise, cotton endowed with resistance to bromoxynil by gene recombination technologies is already marketed under the trade name of BXN.

The above-described "plants" include also plants endowed with a capacity of synthesizing selective toxins known, for example, as genus *Bacillus* and the like by using gene recombination technologies.

Toxins expressed in such gene recombinant plants include insecticidal proteins derived from *Bacillus cereus* and *Bacillus popilliae*; δ-endotoxins such as Cry1Ab, Cry1Ac, Cry1F, Cry1Fa2, Cry2Ab, Cry3A, Cry3Bb1, Cry9C and the like derived from *Bacillus thuringiensis*; insecticidal proteins such as VIP1, VIP2, VIP3, VIP3A and the like; nematode-derived insecticidal proteins; toxins produced by animals such as scorpion toxin, spider toxin, bee toxin, insect-specific neurotoxins and the like; filamentous fungi toxins; plant lectin; agglutinin; protease inhibitors such as trypsin inhibitor, serine protease inhibitor, patatin, cystatin, papain inhibitor and the like; ribosome inactivation proteins (RIP) such as lysine, corn-RIP, abrin, luffin, saporin, briodin and the like; steroid metabolizing enzymes such as 3-hydroxy steroid oxidase, ecdysteroid-UDP-glucosyltransferase, cholesterol oxidase and the like; ecdysone inhibitors; HMG-CoA reductases; ion channel inhibitors such as a sodium channel inhibitor, calcium channel inhibitor and the like; juvenile hormone esterase; diuretic hormone receptor; stilbene synthase; bibenzyl synthase; chitinase; glucanase and the like.

Toxins expressed in such gene recombinant plants include also hybrid toxins, partially deficient toxins and modified toxins of δ-endotoxin proteins such as Cry1Ab, Cry1Ac, Cry1F, Cry1Fa2, Cry2Ab, Cry3A, Cry3Bb1, Cry9C, Cry34Ab, Cry35Ab and the like; insecticidal proteins such as VIP1, VIP2, VIP3, VIP3A and the like. Hybrid toxins are produced by a new combination of different domains of these proteins using a recombination technology. As the partially deficient toxin, Cry1Ab in which a part of an amino acid sequence is deficient is known. In the modified toxin, one or more of amino acids in a natural-type toxin are substituted.

Examples of these toxins and recombinant plants capable of synthesizing these toxins are described in EP-A-0374 753, WO 93/07278, WO 95/34656, EP-A-0 427 529, EP-A-451 878, WO 03/052073 and the like.

Toxins contained in these recombinant plants provide a plant with resistance, particularly, to coleopterous harmful insects, hemipterous harmful insects, dipterous harmful insects, lepidopterous harmful insects and nematodes.

Gene recombinant plants containing one or more insecticidal harmful insect-resistant genes and expressing one or more toxins are already known, and some of them are commercially marketed. Examples of these gene recombinant plants include Yield Gard (registered trademark) (corn plant variety expressing Cry1Ab toxin), Yield Gard Rootworm (registered trademark) (corn plant variety expressing Cry3Bb1), Yield Gard Plus (registered trademark) (corn plant variety expressing Cry1Ab and Cry3Bb1 toxins), Herculex I (registered trademark) (corn plant variety expressing phosphinothricin N-acetyltransferase (PAT) for imparting resistance to Cry1Fa2 toxin and glufosinate), NuCOTN33B (registered trademark) (cotton plant variety expressing Cry1Ac), Boligard I (registered trademark) (cotton plant variety expressing Cry1Ac), Bollgard II (registered trademark) (cotton plant variety expressing Cry1Ac and Cry2Ab), VIPCOT (registered trademark) (cotton plant variety expressing VIP toxin), New Leaf (registered trademark) (potato plant variety expressing Cry3A), Nature Gard (registered trademark), Agrisure (registered trademark), GT Advantage (GA21 glyphosate-resistant character), Agrisure (registered trademark) CB Advantage (Btll cone borer (CB) character), Protecta (registered trademark) and the like.

The above-described "plants" also include plants endowed with a capacity of producing an anti-pathogenic substance having a selective action, using a gene recombination technology.

As examples of the anti-pathogenic substance, PR proteins and the like are known (PRPs, EP-A-0392 225). Such anti-pathogenic substances and gene recombinant plants producing them are described in EP-A-0 392 225, WO 95/33818, EP-A-0 353 191 and the like.

Examples of the anti-pathogenic substance to be expressed in such gene recombinant plants include ion channel inhibitors such as a sodium channel inhibitor, calcium channel inhibitor (KP1, KP4, KP6 toxins and the like produced by virus) and the like; stilbene synthase; bibenzyl synthase; chitinase; glucanase; PR proteins; anti-pathogenic substances produced by microorganisms such as peptide antibiotics, antibiotics having a heterocyclic ring, protein factors correlated with plant disease resistance (referred to as plant disease resistant gene, and described in WO 03/000906) and the like. Such anti-pathogenic substances and gene recombinant plants producing them are described in EP-A-0392225, WO 95/33818, EP-A-0353191 and the like.

The above-described "plants" include also plants endowed with useful characters such as an oil component modifying character, amino acid content enhancing character and the like, using a gene recombination technology. Examples thereof include VISTIVE (registered trademark) (low linolenic soybean having reduced linolenic acid content), high-lysine (high-oil) corn (corn having increased lysine or oil content), and the like.

Further, also included are stacked plant varieties obtained by combination of some of the above-described classical herbicide characters or herbicide-resistant genes, insecticidal harmful insect-resistant genes, anti-pathogenic substance producing genes, useful characters such as an oil component modifying character, amino acid content enhancing character and the like.

Examples of plant diseases which can be controlled by the composition of the present invention include the following diseases. The composition of the present invention shows a particularly excellent control effect on Gray mold; Sclerotnia rot, Stem rot, White mold; and Powdery mildew, of various crops.

Paddy diseases: *Magnaporthe grisea, Cochliobolus miyabeanus, Rhizoctonia solani, Gibberella fujikuroi.*

Wheat diseases: *Erysiphe graminis, Fusarium graminearum, F. avenacerum, F. culmorum, Microdochium nivale, Puccinia striiformis, P. graminis, P. recondite, P. hordei, Typhula* sp., *Micronectriella nivalis, Ustilago tritici, U. nuda, Tilletia caries, Pseudocercosporella herpotrichoides, Rhynchoaporium secalis, Septoria tritici, Leptosphaeria nodorum, Pyrenophora teres* Drechsler.

Citrus diseases: *Diaporthe citri, Elsinoe fawcetti, Penicillium digitatum, P. italicum, Phytophthora parasitica (Phytophthora citrophthora).*

Apple diseases: *Monilinia mali, Valsa ceratosperma, Podosphaera leucotricha, Alternaria alternata* apple pathotype, *Venturia inaequalis, Colletotrichum acutatum, Phytophtora cactorum.*

Pear diseases: *Venturia nashicola, V. pirina, Alternaria alternata* Japanese pear pathotype, *Gymnosporangium haraeanum, Phytophtora cactorum;*

Peach diseases: *Monilinia fructicola, Cladosporium carpophilum, Phomopsis* sp.

Grape diseases: *Elsinoe ampelina, Glomerella cingulata, Uncinula necator, Phakopsora ampelopsidis, Guignardia bidwellii, Plasmopara viticola.*

Persimmon diseases: *Gloeosporium kaki, Cercospora kaki, Mycosphaerella nawae.*

Gourd diseases: *Colletotrichum lagenarium, Sphaerotheca fuliginea, Mycosphaerella melonis, Fusarium oxysporum, Pseudoperonospora cubensis, Phytophthora* SP., *Pythium* sp.;

Tomato diseases: *Alternaria solani, Cladosporium fulvum, Phytophthora infestans.*

Eggplant diseases: *Phomopsis vexans, Erysiphe cichoracearum.*

Brassicaceous vegetable diseases: *Alternaria japonica, Cercosporella brassicae, Plasmodiophora brassicae, Peronospora parasitica.*

Welsh onion diseases: *Puccinia allii, Peronospora destructor.*

Soybean diseases: *Cercospora kikuchii, Elsinoe glycines, Diaporthe phaseolorum* var. *sojae, Phakopsora pachyrhizi, Phytophthora sojae.*

Kidney bean diseases: *Colletotrichum lindemthianum.*

Peanut diseases: *Cercospora personata, Cercospora arachidicola, Sclerotium rolfsii.*

Pea diseases: *Erysiphe pisi.*

Potato diseases: *Alternaria solani, Phytophthora infestans, Phytophthora erythroseptica, Spongospora subterranean* f. sp. *Subterranean.*

Strawberry diseases: *Sphaerotheca humuli, Glomerella cingulata.*

Tea plant diseases: *Exobasidium reticulatum, Elsinoe leucospila, Pestalotiopsis* sp., *Colletotrichum theae-sinensis.*

Tobacco diseases: *Alternaria longipes, Erysiphe cichoracearum, Colletotrichum tabacum, Peronospora tabacina, Phytophthora nicotianae.*

Beet diseases: *Cercospora beticola, Thanatephorus cucumeris, Thanatephorus cucumeris, Aphanomyces cochlioides.*

Rose diseases: *Diplocarpon rosae, Sphaerotheca pannosa, Peronospora sparsa.*

Diseases of chrysanthemum and asteraceae: *Bremia lactucae, Septoria chrysanthemi-indici, Puccinia horiana.*

Diseases of various plants: diseases caused by *pythium* germ; *Pythium aphanidermatum, Pythium debarianum, Pythium graminicola, Pythium irregulare, Pythium ultimum, Botrytis cinerea, Sclerotinia sclerotiorum.*

Radish diseases: *Alternaria brassicicola.*

Zoysia diseases: *Sclerotinia homeocarpa, Rhizoctonia solani.*

Banana diseases: *Mycosphaerella fijiensis, Mycosphaerella musicola.*

Sunflower diseases: *Plasmopara halstedii.*

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp. and the like.

Virus diseases of various plants mediated by *Polymixa* spp., *Olpidium* spp. or the like.

In the composition of the present invention, Group A and Group B are mixed at a proportion of usually 1:0.0625 to 1:20, preferably 1:0.125 to 1:20, further preferably 1:0.25 to 1:4, the weight of Group A being 1.

For producing the composition of the present invention, it is usual that a mixture of Group A and Group B (hereinafter, referred to as present active ingredient) is mixed with an inert carrier such as a solid carrier, liquid carrier, gas carrier and the like, and if necessary, a surfactant, other auxiliaries for formulation such as a fixing agent, dispersant, stabilizer and the like are added, and these are formulated into a wettable powder, water dispersible granule, flowable formulation, granule, dry flowable formulation, emulsion, aqueous liquid formulation, oil formulation, smoking agent, aerosol, microcapsule and the like. These formulations contain the present active ingredient at a weight ratio of usually 0.1 to 99%, preferably 0.2 to 90%.

Examples of the solid carrier include fine powders or granular materials of clays (for example, kaolin, diatomaceous earth, synthetic water-containing silicon oxide, Fubasami clay, bentonite, acid clay), talcs, other inorganic minerals (for example, sericite, quartz powder, sulfur powder, activated carbon, calcium carbonate, hydrated silica) and the like. Examples of the liquid carrier include water, alcohols (e.g., methanol, ethanol), ketones (e.g., acetone, methyl ethyl ketone), aromatic hydrocarbons (e.g., benzene, toluene, xylene, ethylbenzene, methylnaphthalen), aliphatic hydrocarbons (e.g., n-hexane, cyclohexane, kerosene), esters (e.g., ethyl acetate, butyl acetate), nitriles (e.g., acetonitrile, isobutyronitrile), ethers (e.g., dioxane, diisopropyl ether), acid amides (e.g., dimethylformamide, dimethylacetamide) and halogenated hydrocarbons (e.g., dichloroethane, trichloroethylene, carbon tetrachloride).

Examples of the surfactant include alkyl sulfate esters, alkyl sulfonate salts, alkyl aryl sulfonate salts, alkyl aryl ethers, and polyoxyethylenated materials thereof, polyoxy ethylene glycol ethers, polyhydric alcohol esters, sugar alcohol derivatives and the like.

Other auxiliaries for preparation include, for example, a fixing agent, dispersant and stabilizer. Specific examples of such auxiliaries for preparation include casein, gelatin, saccharides (e.g., starch, gum arabic, cellulose derivatives, alginic acid), lignin derivatives, bentonite, sugars, synthetic water-soluble polymers (e.g., polyvinyl alcohol, polyvinyl pyrrolidone, polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oil, fatty acids and fatty esters.

The composition of the present invention can also be prepared by mixing a formulation of Group A and a formulation of Group B.

The control method of the present invention is performed by applying Group A and Group B, as an active ingredient, to a plant or the soil where a plant is grown. Examples of the method of applying an active ingredient to a plant include a method in which an active ingredient is applied to stems and leaves of a plant and a method in which an active ingredient is applied to plant seeds.

The control method of the present invention is carried out, for example, by applying a mixture of Group A and Group B to a plant or the soil where a plant is grown, simultaneously applying Group A and Group B to a plant or the soil where a plant is grown, or sequentially applying Group A and Group B to a plant or the soil where a plant is grown.

In the control method of the present invention, when the active ingredient is applied to stems and leaves of a plant or when the active ingredient is applied to the soil where a plant is grown, the amount of the active ingredient to be applied is usually 1 to 500 g, preferably 2 to 200 g, in terms of the total amount of Group A and Group B per 1000 m² of the area to be applied. In the control method of the present invention, when the active ingredient is applied to stems and leaves of a plant or when the active ingredient is applied to the soil where a plant is grown, an emulsion, wettable powder, suspending agent and the like are usually diluted with water before the application, and in this case, the concentration of all active ingredients is usually 0.0005 to 2%, preferably 0.005 to 1%. A powder, granule and the like are usually used as they are without dilution.

In the control method of the present invention, when the active ingredient is applied to plant seeds, the amount of the active ingredient to be applied is usually 0.001 to 100 g, preferably 0.01 to 50 g per 1 kg of seeds, in terms of the total amount of Group A and Group B. The method of applying an active ingredient to plant seeds includes, for example, a method of dust-coating seeds with a formulation containing an active ingredient, a method of immersing seeds in a formulation containing an active ingredient, and a method of coating seeds with a carrier containing an active ingredient.

EXAMPLES

The present invention will be illustrated further in detail by formulation examples and test examples below, but the present invention is not limited only to the following examples. In the following example, parts are by weight unless otherwise stated.

The compound (Ia) is a compound of the following formula (Ia).

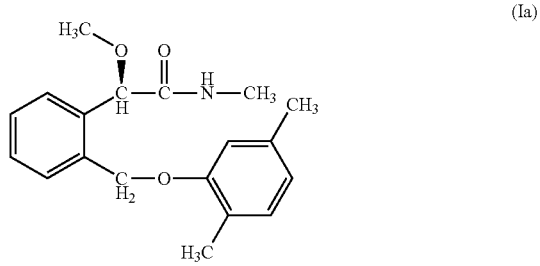 [SMILES: CNC(=O)[C@H](OC)c1ccccc1COc1cc(C)ccc1C]

(Ia)

The compound (Ib) is a compound of the following formula (Ib).

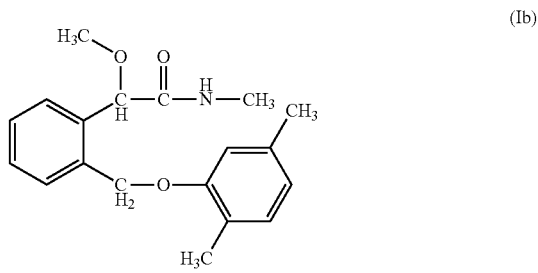 [SMILES: CNC(=O)C(OC)c1ccccc1COc1cc(C)ccc1C]

(Ib)

Formulation Example 1

A compound (Ia) or a compound (Ib) (2.5 parts), a compound (II) (1.25 parts), polyoxyethylene styrylphenyl ether (14 parts), calcium dodecylbenzenesulfonate (6 parts) and xylene (76.25 parts) are thoroughly mixed to obtain respective emulsions.

Formulation Example 2

A compound (Ia) or a compound (Ib) (5 parts), a compound (III) (5 parts), a mixture (35 parts) of white carbon and polyoxyethylene alkyl ether sulfate ammonium salt (weight ratio 1:1) and water (55 parts) are mixed, and finely ground by a wet grinding method to obtain respective flowable formulations.

Formulation Example 3

A compound (Ia) or a compound (Ib) (5 parts), a compound (IV) (10 parts), sorbitan trioleate (1.5 parts) and an aqueous solution (28.5 parts) containing 2 parts of polyvinyl alcohol are mixed, and finely ground by a wet grinding method, then, into this is added an aqueous solution (45 parts) containing xanthan gum (0.05 parts) and 0.1 part of aluminum magnesium silicate, further, propylene glycol (10 parts) is added and mixed with stirring, to obtain respective flowable formulations.

Formulation Example 4

A compound (Ia) or a compound (Ib) (1 part), a compound (II) (4 parts), synthetic water-containing silicon oxide (1 part), calcium ligninsulfonate (2 parts), bentonite (30 parts) and kaolin clay (62 parts) are thoroughly ground and mixed, and water is added to this and the mixture is thoroughly kneaded, then, granulated and dried to obtain respective granules.

Formulation Example 5

A compound (Ia) or a compound (Ib) (12.5 parts), a compound (III) (37.5 parts), calcium ligninsulfonate (3 parts), sodium laurylsulfate (2 parts) and synthetic water-containing silicon oxide (45 parts) are thoroughly ground and mixed to obtain respective wettable powders.

Formulation Example 6

A compound (Ia) or a compound (Ib) (1 part), a compound (IV) (2 parts), kaolin clay (85 parts) and talc (10 parts) are thoroughly ground and mixed to obtain respective powders.

Formulation Example 7

A compound (Ia) or a compound (Ib) (2 parts), a compound (IV) (0.25 parts), polyoxyethylene styrylphenyl ether (14 parts), calcium dodecylbenzenesulfonate (6 parts) and xylene (77.75 parts) are thoroughly mixed to obtain respective emulsions.

Formulation Example 8

A compound (Ia) or a compound (Ib) (10 parts), a compound (IV) (2.5 parts), sorbitan trioleate (1.5 parts) and an aqueous solution (30 parts) containing 2 parts of polyvinyl alcohol are mixed, and finely ground by a wet grinding method, then, into this is added and an aqueous solution (47.5 parts) containing xanthan gum (0.05 parts) 0.1 part of aluminum magnesium silicate, further, propylene glycol (10 parts) is added and mixed with stirring, to obtain respective flowable formulations.

Formulation Example 9

A compound (Ia) or a compound (Ib) (1 part), a compound (II) (20 parts), synthetic water-containing silicon oxide (1 part), calcium ligninsulfonate (2 parts), bentonite (30 parts) and kaolin clay (47 parts) are thoroughly ground and mixed, and water is added to this and the mixture is thoroughly kneaded, then, granulated and dried to obtain respective granules.

Formulation Example 10

A compound (Ia) or a compound (Ib) (4.5 parts), a compound (III) (45 parts), calcium ligninsulfonate (3 parts), sodium laurylsulfate (2 parts) and synthetic water-containing silicon oxide (45.5 parts) are thoroughly ground and mixed to obtain respective wettable powders.

Test Example 1

A plastic pot was stuffed with sand loam, and cucumber was sowed, and grown for 12 days in a greenhouse. A compound (Ia), compound (Ib) and compound (II) were prepared into flowable formulations according to the following preparation method, and the resultant flowable formulations were diluted with water, then, mixed to prepare a treatment solution containing the compound (Ia) and compound (II) of prescribed concentrations, and a treatment solution containing the compound (Ib) and compound (II) of prescribed concentrations. The treatment solutions were sprayed on stems and leaves so as to fully adhere to the leaf surfaces of the cucumber. After spraying, the plant was air-dried, and a PDA medium containing spores of cucumber Gray mold fungus was placed on the cucumber leaf surface. Thereafter, it was left for 6 days at 12° C. under humid condition, then, a control effect thereof was checked.

Further, wettable powders of the compound (Ia), compound (Ib) and compound (II) each were diluted with water to prescribed concentrations to prepare respective treatment solutions, which were subjected to a parallel test.

In checking, evaluation indices described later were used. According to formula 1, the pathogenesis degree was calculated, and based on the pathogenesis degree, a controlling value (%) was calculated using formula 2.

Preparation Method

A compound (Ia), compound (Ib) or compound (II) (10 parts), a mixture (35 parts) of white carbon and polyoxyethylene alkyl ether sulfate ammonium salt (weight ratio 1:1) and water (55 parts) were mixed, and finely ground by a wet grinding method to obtain respective flowable formulations.

The results are shown in Table 1.

Evaluation Indices
0: disease spot diameter, 0 mm
1: disease spot diameter, 1 to 5 mm
2: disease spot diameter, 5 to 10 mm
3: disease spot diameter, 10 to 15 mm
4: disease spot diameter, 15 to 20 mm
5: disease spot diameter, over 20 mm pathogenesis degree=Σ(evaluation index of checked leaf)×100/(5×number of checked leaves)   Formula 1 controlling value (%)=100×(A−B)/A   Formula 2

A: pathogenesis degree of plant in non-treated district
B: pathogenesis degree of plant in treated district

TABLE 1

| Tested compound | active ingredient concentration (ppm) | controlling value |
|---|---|---|
| compound (Ia) + compound (II) | 20 + 10 | 100 |
| compound (Ia) + compound (II) | 10 + 10 | 100 |
| compound (Ia) + compound (II) | 2.5 + 10 | 88 |
| compound (Ib) + compound (II) | 40 + 10 | 100 |
| compound (Ib) + compound (II) | 20 + 10 | 100 |
| compound (Ib) + compound (II) | 5 + 10 | 88 |
| compound (Ia) | 20 | 68 |
| compound (Ia) | 10 | 60 |
| compound (Ia) | 2.5 | 48 |
| compound (Ib) | 40 | 68 |
| compound (Ib) | 20 | 60 |
| compound (Ib) | 5 | 48 |
| compound (II) | 10 | 30 |

Test Example 2

A plastic pot was stuffed with sand loam, and cucumber was sowed, and grown for 12 days in a greenhouse. A compound (Ia), compound (Ib), compound (III) and compound (IV) were prepared into flowable formulations according to the following preparation method, and the resultant flowable formulations were diluted with water, then, mixed to prepare a treatment solution containing the compound (Ia) and compound (III) of prescribed concentrations, a treatment solution containing the compound (Ib) and compound (III) of prescribed concentrations, a treatment solution containing the compound (Ia) and compound (IV) of prescribed concentrations, and a treatment solution containing the compound (Ib) and compound (IV) of prescribed concentrations. The treatment solutions were sprayed on stems and leaves so as to fully adhere to the leaf surfaces of the cucumber. After spraying, the plant was air-dried, and a PDA medium containing spores of cucumber Gray mold fungus was placed on the cucumber leaf surface. Thereafter, it was left under humid condition at 12° C., then, a control effect thereof was checked.

Further, wettable powders of the compound (Ia), compound (Ib), compound (III) and compound (IV) each were diluted with water to prescribed concentrations to prepare respective treatment solutions, which were subjected to a parallel test.

In checking of the control effect, the disease spot diameter was measured for 8 leaves of cucumber. A case of a disease spot diameter of 0 mm was evaluated as a controlling index of 0, a case of a disease spot diameter of 1 to 5 mm was evaluated as a controlling index of 1, a case of a disease spot diameter of 5 to 10 mm was evaluated as a controlling index of 2, a case of a disease spot diameter of 10 to 15 mm was evaluated as a controlling index of 3, a case of a disease spot diameter of 15 to 20 mm was evaluated as a controlling index of 4, and a case of a disease spot diameter of over 20 mm was evaluated as a controlling index of 5. The sum of the controlling indices of eight cucumber leaves measured is shown in Table 2.

Preparation Method

A compound (Ia), compound (Ib), compound (III) or compound (IV) (10 parts), a mixture (35 parts) of white carbon and polyoxyethylene alkyl ether sulfate ammonium salt (weight ratio 1:1) and water (55 parts) were mixed, and finely ground by a wet grinding method to obtain respective flowable formulations.

TABLE 2

|  | active ingredient concentration (ppm) | sum of controlling indices |
|---|---|---|
| compound (Ia) + compound (III) | 20 + 5 | 0 |
| compound (Ia) + compound (III) | 10 + 5 | 0 |
| compound (Ia) + compound (III) | 5 + 5 | 0 |
| compound (Ia) + compound (III) | 2.5 + 5 | 0 |
| compound (Ib) + compound (III) | 40 + 5 | 0 |
| compound (Ib) + compound (III) | 20 + 5 | 0 |
| compound (Ib) + compound (III) | 10 + 5 | 0 |
| compound (Ib) + compound (III) | 5 + 5 | 0 |
| compound (Ia) + compound (IV) | 20 + 2.5 | 3 |
| compound (Ia) + compound (IV) | 20 + 5 | 0 |
| compound (Ia) + compound (IV) | 10 + 2.5 | 4 |
| compound (Ia) + compound (IV) | 10 + 5 | 0 |
| compound (Ia) + compound (IV) | 5 + 2.5 | 2 |
| compound (Ia) + compound (IV) | 5 + 5 | 0 |
| compound (Ia) + compound (IV) | 2.5 + 2.5 | 3 |
| compound (Ia) + compound (IV) | 2.5 + 5 | 0 |
| compound (Ib) + compound (IV) | 40 + 2.5 | 4 |
| compound (Ib) + compound (IV) | 40 + 5 | 0 |
| compound (Ib) + compound (IV) | 20 + 2.5 | 5 |
| compound (Ib) + compound (IV) | 20 + 5 | 0 |
| compound (Ib) + compound (IV) | 10 + 2.5 | 5 |
| compound (Ib) + compound (IV) | 10 + 5 | 0 |
| compound (Ib) + compound (IV) | 5 + 2.5 | 6 |
| compound (Ib) + compound (IV) | 5 + 5 | 0 |
| compound (Ia) | 20 | 23 |
| compound (Ia) | 10 | 24 |
| compound (Ia) | 5 | 25 |
| compound (Ia) | 2.5 | 27 |
| compound (Ib) | 40 | 24 |
| compound (Ib) | 20 | 24 |
| compound (Ib) | 10 | 26 |
| compound (Ib) | 5 | 25 |
| compound (III) | 5 | 10 |
| compound (IV) | 2.5 | 24 |
| compound (IV) | 5 | 9 |

INDUSTRIAL APPLICABILITY

The composition of the present invention has an excellent plant disease control effect.

The invention claimed is:

1. A plant disease control composition comprising Group A and Group B as an active ingredient, wherein:

Group A is
a compound of formula (I) or a salt thereof:

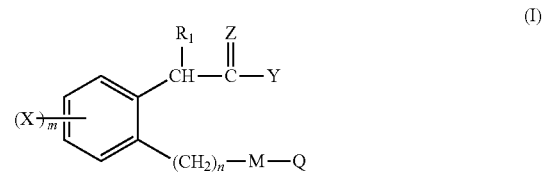

wherein, $R_1$ represents a halogen atom, optionally substituted alkyl group, optionally substituted hydroxyl group, alkylthio group, alkylsulfinyl group, alkylsulfonyl group, optionally substituted amino group or nitro group, Q represents an optionally substituted aryl group, optionally substituted heterocyclic group, mono- or di-substituted methyleneamino group, optionally substituted methyl group, optionally substituted (substituted imino) methyl group, optionally substituted alkyl group, optionally substituted alkenyl group, optionally substituted alkynyl group, substituted formyl group or substituted sulfonyl group, X represents a halogen atom, optionally substituted alkyl group or optionally substituted hydroxyl group, Y represents an optionally substituted hydroxyl group, alkylthio group or optionally substituted amino group, with the proviso that when $R_1$ represents a hydroxyl group, then, Y is not an alkoxy group, Z represents an oxygen atom or sulfur atom, M represents an oxygen atom, $S(O)_I$, wherein I represents 0, 1 or 2, $NR_2$, wherein $R_2$ represents a hydrogen atom, alkyl group or acyl group, or single bond, n represents 0, 1 or 2, m represents 0, 1, 2 or 3;

Group B is
one or more anilinopyrimidine compounds selected from the group consisting of 4,6-dimethyl-N-phenyl-2-pyrimidinamine, 4-methyl-N-phenyl-6-(1-propynyl)-2-pyrimidinamine and 4-cyclopropyl-6-methyl-N-phenyl-2-pyrimidinamine.

2. The plant disease control composition according to claim 1, wherein Group A is a compound of formula (I) or a salt thereof, and in the compound of formula (I), $R_1$ represents a halogen atom, or a hydroxyl group optionally substituted with a C1 to C4 alkyl group or C1 to C4 haloalkyl group, Q represents a phenyl group optionally substituted with one or more of halogen atoms, methyl groups, trifluoromethyl groups or methoxy groups, Y represents an amino group optionally substituted with one or more of C1 to C3 alkyl groups, Z represents an oxygen atom, M represents an oxygen atom, n represents 1, m represents 0.

3. The plant disease control composition according to claim 1, wherein Group A is a compound of formula (I) or a salt thereof, and in the compound of formula (I), $R_1$ represents a methoxy group, Q represents a 2,5-dimethylphenyl group, Y represents a monomethylamino group, Z represents an oxygen atom, M represents an oxygen atom, n represents 1, m represents 0.

4. The plant disease control composition according to claim 1, wherein Group B is 4,6-dimethyl-N-phenyl-2-pyrimidinamine.

5. The plant disease control composition according to claim 1, wherein Group B is 4-methyl-N-phenyl-6-(1-propynyl)-2-pyrimidinamine.

6. The plant disease control composition according to claim 1, wherein Group B is 4-cyclopropyl-6-methyl-N-phenyl-2-pyrimidinamine.

7. The plant disease control composition according to claim 1, wherein the weight ratio of Group A to Group B is in the range from 0.125:1 to 20:1.

8. A plant disease control method comprising applying Group A and Group B to a plant or the soil where a plant is grown, wherein:

Group A is a compound of formula (I) or a salt thereof:

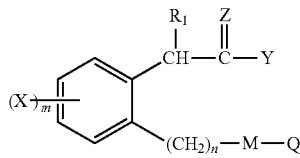
(I)

wherein, $R_1$ represents a halogen atom, optionally substituted alkyl group, optionally substituted hydroxyl group, alkylthio group, alkylsulfinyl group, alkylsulfonyl group, optionally substituted amino group or nitro group, Q represents an optionally substituted aryl group, optionally substituted heterocyclic group, mono- or di-substituted methyleneamino group, optionally substituted methyl group, optionally substituted (substituted imino) methyl group, optionally substituted alkyl group, optionally substituted alkenyl group, optionally substituted alkynyl group, substituted formyl group or substituted sulfonyl group, X represents a halogen atom, optionally substituted alkyl group or optionally substituted hydroxyl group, Y represents an optionally substituted hydroxyl group, alkylthio group or optionally substituted amino group, with the proviso that when $R_1$ represents a hydroxyl group, then, Y is not an alkoxy group, Z represents an oxygen atom or sulfur atom, M represents an oxygen atom, $S(O)_I$, wherein I represents 0, 1 or 2, $NR_2$, wherein $R_2$ represents a hydrogen atom, alkyl group or acyl group, or single bond, n represents 0, 1 or 2, m represents 0, 1, 2 or 3;

Group B is one or more anilinopyrimidine compounds selected from the group consisting of 4,6-dimethyl-N-phenyl-2-pyrimidinamine, 4-methyl-N-phenyl-6-(1-propynyl)-2-pyrimidinamine and 4-cyclopropyl-6-methyl-N-phenyl-2-pyrimidinamine.

9. The plant disease control method according to claim 8, wherein Group A is a compound of formula (I) or a salt thereof, and in the compound of formula (I), $R_1$ represents a halogen atom, or a hydroxyl group optionally substituted with a C1 to C4 alkyl group or C1 to C4 haloalkyl group, Q represents a phenyl group optionally substituted with one or more of halogen atoms, methyl groups, trifluoromethyl groups or methoxy groups, Y represents an amino group optionally substituted with one or more of C1 to C3 alkyl groups, Z represents an oxygen atom, M represents an oxygen atom, n represents 1, m represents 0.

10. The plant disease control method according to claim 8, wherein Group A is a compound of formula (I) or a salt thereof, and in the compound of formula (I), $R_1$ represents a methoxy group, Q represents a 2,5-dimethylphenyl group, Y represents a monomethylamino group, Z represents an oxygen atom, M represents an oxygen atom, n represents 1, m represents 0.

11. The plant disease control method according to claim 8, wherein Group B is 4,6-dimethyl-N-phenyl-2-pyrimidinamine.

12. The plant disease control method according to claim 8, wherein Group B is 4-methyl-N-phenyl-6-(1-propynyl)-2-pyrimidinamine.

13. The plant disease control method according to claim 8, wherein Group B is 4-cyclopropyl-6-methyl-N-phenyl-2-pyrimidinamine.

14. The plant disease control method according to claim 8, wherein the weight ratio of Group A to Group B is in the range from 0.125:1 to 20:1.

* * * * *